United States Patent [19]

Fischer et al.

[11] 3,997,531
[45] Dec. 14, 1976

[54] 2,1,3-BENZOTHIADIAZIN-(4)-ONE-2,2-DIOXIDES

[75] Inventors: Adolf Fischer, Mutterstadt; Karl-Heinz Koenig, Frankenthal; Gerhard Hamprecht, Mannheim, all of Germany

[73] Assignee: BASF Aktiengesellschaft, Ludwigshafen (Rhine), Germany

[22] Filed: Sept. 16, 1974

[21] Appl. No.: 506,559

[30] Foreign Application Priority Data

Sept. 29, 1973 Germany .......................... 2349114

[52] U.S. Cl. .................................. 260/243 R; 71/91
[51] Int. Cl.$^2$ ...................................... C07D 285/16

[58] Field of Search ................................. 260/243 R

[56] References Cited

UNITED STATES PATENTS 3,822,257   7/1974   Hamprecht et al. ............... 260/243

*Primary Examiner*—John M. Ford

[57] ABSTRACT

New and valuable 2,1,3-benzothiadiazin-(4)-one-2,2-dioxides having a good herbicidal action and a process for controlling the growth of unwanted plants with these compounds.

2 Claims, No Drawings

2,1,3-BENZOTHIADIAZIN-(4)-ONE-2,2-DIOXIDES

The present invention relates to new and valuable substituted 2,1,3-benzothiadiazin-(4)-one-2,2-dioxides having a herbicidal action, herbicides containing these compounds as active ingredients, and a process for controlling the growth of unwanted plants with these compounds.

It is known to use 3-isopropyl-2,1,3-benzothiadiazin-(4)-one-2,2-dioxide as a herbicidal active ingredient. However, it was not known that there are compounds in this group of substances which, in addition to combatting dicotyledonous plants, also control the growth of monocotyledonous plants, especially barnyardgrass, without damaging crop plants.

We have now found that 2,1,3-benzothiadiazin-(4)-one-2,2-dioxides of the formula

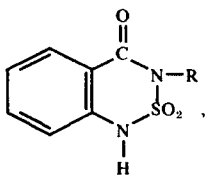

where R denotes hydrogen, a cycloaliphatic radical of 3, 4, 5 or 7 carbon atoms, sec-butyl, tert-butyl, a branched aliphatic radical of 5 to 10 carbon atoms or a halogen-substituted aliphatic radical of 2 to 10 carbon atoms, or a salt thereof, e.g., the metal salts or the salts of unsubstituted or substituted amines, have better crop plant compatibility than the comparative agent, combined with the same herbicidal action, particularly on grassy weeds.

The new compounds may be prepared by known methods. Suitable starting materials are, for example, anthranilic acid, its esters, and 1H-2,1,3-benzothiadiazin-4-(3H)-one-2,2-dioxide (E. Cohen and B. Klarberg, J. Am. Chem. Soc., 84, 1994, 1962). The reaction of anthranilic acid or its esters with alkylaminosulfonyl chlorides to give sulfamides, their cyclization to 2,1,3-benzothiadiazin-(4)-one-2,2-dioxides, and alkyl- and haloalkylaminosulfonyl halides are described in German Laid-Open Applications (DOS) 2,104,682; 2,105,687; 2,164,176; and 2,164,197.

EXAMPLE 1

3-sec-butyl-2,1,3-benzothiadiazin-(4)-one-2,2-dioxide

At 20° C, 59.3 parts (by weight) of sec-butylaminosulfonyl chloride and 41.9 parts of dimethylcyclohexylamine are simultaneously added, while stirring, to a suspension of 47.3 parts of anthranilic acid in 8.6 parts of dimethylformamide (DMF) and 240 parts of chlorobenzene. After the mixture has been stirred for 1 hour 2 parts of DMF is added and 79 parts of phosgene is introduced at 30° to 40° C. The solution is stirred for a further 2 hours at 40° C. The excess phosgene is removed and the solution is extracted first with 150 parts of ice water and then with 200 parts of 3N caustic solution. The alkaline extract is extracted twice with 50 parts of methylene chloride and then stirred into dilute sulfuric acid. After suction filtration, washing with water amd drying at 50° C, the desired compound is obtained in the form of colorless crystals; m.p.: 107° to 108° C.

A recrystallized sample melts at 112° to 114° C. The product has the following formula:

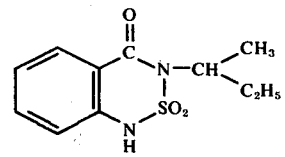

The sodium salt is obtained by dissolving 2.0 parts of sodium hydroxide and 12.5 parts of 3-sec-butyl-2,1,3-benzothiadiazin-(4)-one-2,2-dioxide in 60 parts of water, and concentration in vacuo; m.p.: 138° to 142° C.

EXAMPLE 2

3-sec-butyl-2,1,3-benzothiadiazin-(4)-one-2,2-dioxide, isopropylammonium salt 2.95 parts of isopropylamine in 20 parts of ether is added, at room temperature, to a solution of 12.5 parts of 3-sec-butyl-2,1,3-benzothiadiazin-(4)-one-2,2-dioxide in 40 parts of ether. The precipitated mass crystallizes upon trituration; m.p.: 119° to 121° C.

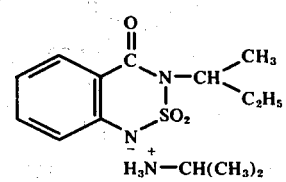

The following compounds were prepared analogously:

| R$^1$ | R$^2$ | m.p. (° C) |
|---|---|---|
| H | ◁H | |
| ⊞–NH$_3^+$ | –CH(C$_2$H$_5$)(CH$_3$) | 172 to 175 |

-continued

[Structure: benzo-fused ring with C=O, N-R², SO₂, N-R¹]

| R¹ | R² | m.p. (° C) |
|---|---|---|
| cyclohexyl-NH₃⁺ | -CH(C₂H₅)(CH₃) | 89 to 92 |
| C₁₂H₂₅NH₃⁺ | -CH(C₂H₅)(CH₃) | viscous oil |
| H | -C(CH₃)₃ | |
| H | [cyclohexyl-H] | |
| H | -CH(CH₃)(CH(CH₃)₂) | 118 to 122 |
| H | -CH₂-CH(C₂H₅)(CH₃) | 120 to 122 |
| Na | -CH₂-CH(C₂H₅)(CH₃) | 139 (decomposes) |
| H | -CH(C₂H₅)(C₂H₅) | 128 to 132 |
| Na | -CH(C₂H₅)(C₂H₅) | 150 to 175 (decomposes) |
| H | cyclopentyl-H | 145 to 147 |
| H | -CH(CH₃)(CH(C₂H₅)CH₃) | 120 to 123 |
| Na | -CH(CH₃)(CH(C₂H₅)CH₃) | 135 to 147 (decomposes) |
| H | -CH(CH₃)(CH₂CH(CH₃)₂) | 122 to 128 |
| Na | -CH(CH₃)(CH₂CH(CH₃)₂) | 190 to 210 |
| H | -CH(C₂H₅)((CH₂)₃CH₃) | viscous oil |
| Na | -CH(C₂H₅)((CH₂)₃CH₃) | 191 to 210 |
| H | -CH(CH₃)(CH(CH₃)(CH₂)₃CH₃) | 112 to 116 |
| H | -CH(CH₃)(cyclohexyl-H) | 160 to 165 |

-continued
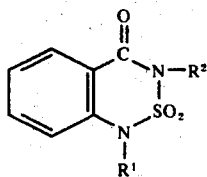
| R¹ | R² | | m.p. (° C) |
|---|---|---|---|
| H | —CH₂—CH₂—Cl | | 165 to 167 |
| H | —CH₂—CH(CH₃)Cl | | 128 to 132 |
| H | —(CH₂)₃Cl | | 139 to 141 |
| H | —CH(CH₃)—CH₂Cl | (86:14) | 105 to 112 |
| H | —CH₂—CHCl—CH₃ | | |
| H | —CH(CH₃)—CH(CH₃)Cl | | |
| H | —CH(C₂H₅)—CH₂—Cl | | 98 to 104 |
| H | —CH₂—C(CH₃)₂—Cl | | 154 to 158 |
| H | —C(CH₃)₂—CH₂Cl | | |
| H | —CH₂—CH₂F | | |
| H | —CH(CH₃)—CH₂F | (33:67) | 97 to 102 |
|   | —CH₂—CH(CH₃)F | | |
| Na | —CH(CH₃)—CH₂F | (33:67) | 113 to 120 (decomposes) |
|   | —CH₂—CH(CH₃)F | | |
| H | —CH₂—C(CH₃)₂—F | | 144 to 146 |
| Na | —CH₂—C(CH₃)₂—F | | 170 to 178 (decomposes) |
| H | —CH(C₂H₅)—CH₂F | | |
| H | —C(CH₃)₂—CH₂F | | |

| R¹ | R² | m.p. (° C) |
|---|---|---|
| H | —CH—CHF<br>    \|    \|<br>   CH₃  CH₃ | |

The new agents have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used fpr controlling for instance Gramineae, such as
  Cynodon spp.
  Digitaria spp.
  Echinochloa spp.
  Setaria spp.
  Panicum spp.
  Alopecurus spp.
  Lolium spp.
  Sorghum spp.
  Agropyron spp.
  Phalaris spp.
  Apera spp.
  etc.;
  Dactylis spp.
  Avena spp.
  Bromus spp.
  Uniola spp.
  Poa spp.
  Leptochloa spp.
  Brachiaria spp.
  Eleusine spp.
  Cenchrus spp.
  Eragrostis spp.
  Phragmitres communis Cyperaceae, such as
  Carex spp.
  Cyperus spp.
  etc.;
  Eleocharis spp.
  Scirpus spp.

dicotyledonous weeds, such as
Malvaceae, e.g.
  Abutilon theoprasti
  Sida spp.
  etc.;
  Hibiscus spp.
  Malva spp.

Compositae, such as
  Ambrosia spp.
  Lactuca spp.
  Senecio spp.
  Sonchus spp.
  Xanthium spp.
  Iva spp.
  Galinsoga spp.
  Taraxacum spp.
  Chrysanthemum spp.
  Cirsium spp.
  Centaurea spp.
  Tussilago spp.
  Lapsana communis
  Tagetes spp.
  Erigeron spp.
  Anthemis spp.
  Matricaria spp.
  Artemisia spp.
  Bidens spp.
  etc.;

Convolvulaceae, such as
  Convolvulus spp.
  Ipomoea spp.
  etc.;
  Cuscuta spp.
  Jaquemontia tamnifolia Cruciferae, such as
  Barbarea vulgaris
  Brassica spp.
  Capsella spp.
  Sisymbrium spp.
  Thlaspi spp.
  Sinapis arvensis
  etc.;
  Arabidopsis thaliana
  Descurainia spp.
  Draba spp.
  Coronopus didymus
  Lepidium spp.
  Raphanus spp.

Geraniaceae, such as
  Erodium spp.
  etc.;
  Geranium spp.

Portulacaceae, such as
  Portulaca spp.
  etc.;

Primulaceae, such as
  Anagallis arvensis
  etc.
  Lysimachia spp.

Rubiaceae, such as
  Richardia spp.
  Galium spp.
  Diodia spp.
  etc.;

Scrophulariaceae, such as
  Linaria spp.
  Veronica spp.
  Digitalis spp.
  etc.;

Solanaceae, such as
  Physalis spp.
  Solanum spp.
  etc.;
  Nicandra spp.
  Datura spp.

Urticaceae, such as
  Urtica spp.

Violaceae, such as
  Viola spp.
  etc.;

Zygophyllaceae, such as
  Tribulus terrestris
  etc.;

Euphorbiaceae, such as
  Mercurialis annua
  Euphorbia spp.

Umbelliferae, such as
  Daucus carota
  Aethusa cynapium
  Ammi majus
  etc.;

Commelinaceae, such as
  Commelina spp.
  etc.;

Labiatae, such as
  Lamium spp.
  etc.;
  Galeopsis spp.

Leguminosae, such as
  Medicago spp.
  Trifolium spp.
  Vicia spp.
  etc.;
  Sesbania exaltata
  Cassia spp.
  Lathyrus spp.

Plantaginaceae, such as
  Plantago spp.
  etc.;

Polygonaceae, such as
  Polygonum spp.
  Rumex spp.
  Fagopyrum spp.
  etc.;

Aizoaceae, such as
  Mollugo verticillata
  etc.;

Amaranthaceae, such as
  Amaranthus spp.
  etc.;

Boraginaceae, such as
  Amsinckia spp.
  Myostis spp.
  etc.;
  Anchusa spp.
  Lithospermum spp.

Caryophyllaceae, such as
  Stellaria spp.
  Spergula spp.
  Saponaria spp.
  Scleranthus annuus
  Silene spp.
  Cerastium spp.
  Agrostemma githago
  etc.;

Chenopodiaceae, such as
  Chenopodium spp.
  Kochia spp.
  Salsola Kali
  Atriplex spp.
  Monolepsis nuttalliana
  etc.;

Lythraceae, such as
  Cuphea spp.
  etc.;

Oxalidaceae, such as
  Oxalis spp.

Ranunculaceae, such as
  Ranunculus spp.
  Delphinium spp.
  Adonis spp.
  etc.;

Papaveraceae, such as
  Papaver spp.
  etc.;
  Fumaria officinalis

Onagraceae, such as
  Jussiaea spp.
  etc.;

Rosaceae, such as
  Alchemilla spp.
  etc.;
  Potentilla spp.

Potamogetonaceae, such as
  Potamogeton spp.
  etc.;

Najadacea, such as
  Najas spp.
  etc.;

Equisetaceae, such as
  Equisetum spp.
  etc.;

Marsileaceae, such as
  Marsilea quadrifolia
  etc.;

| -continued | |
|---|---|
| Polypodiaceae, such as Pteridium quilinum | |
| Alismataceae, such as Alisma spp. etc. | Sagittaria sagittifolia |

The amount used of the agents according to the invention may vary and depends in essence on the type of effect to be achieved; it is generally from 0.1 to 15 (and more), preferably from 0.2 to 6, kg per hectare of active ingredient.

The compositions may be used in cereal crops such as

| Avena spp. | Sorghum |
|---|---|
| Triticum spp. | Zea mays |
| Hordeum spp. | Panicum miliaceum |
| Secale spp. | Oryza spp. |
| Saccharum officinarum | |
| and in dicotyledonous crops such as | |
| Cruciferae, e.g. | |
| Brassica spp. | Raphanus spp. |
| Sinapis spp. | Lepidium spp. |
| Compositae, e.g. | |
| Lactuca spp. | Carthamus spp. |
| Helianthus spp. | Scorzonera spp. |
| Malvaceae, e.g. | |
| Gossypium hirsutum | |
| Leguminosae, e.g. | |
| Medicago, spp. | Phaseolus spp. |
| Trifolium spp. | Arachis spp. |
| Pisum spp. | Glycine max. |
| Chenopodiaceae, e.g. | |
| Beta vulgaris | Spinacia spp. |
| Solanaceae, e.g. | |
| Solanum spp. | Capsicum annuum |
| Nicotiania spp. | |
| Linaceae, e.g. | |
| Linum spp. | |
| Umbelliferae, e.g. | |
| Petroselinum spp. | Apium graveolens |
| Daucus carota | |
| Rosaceae, e.g. | |
| Fragaria | |
| Cucurbitaceae, e.g. | |
| Cucumis spp. | Cucurbita spp. |
| Liliaceae, e.g. | |
| Allium spp. | |
| Vitaceae, e.g. | |
| Vitis vinifera | |
| Bromeliaceae, e.g. | |
| Annas sativus. | |

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, arkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts or sulfated hexadecanols, heptadecanols, and octadecanols, salts or sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctyphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

There may be added to the compositions or individual active ingredients (if desired, immediately before use (tank-mix)) oils of various types, herbicides, fungicides, nematocides, insecticides, bactericides, trace elements, fertilizers, antifoams (e.g., siliocones), growth regulators antidotes, and other herbicidally effective compounds such as
substituted anilines
substituted aryloxycarboxylic acids and salts, esters and amides thereof
substituted ethers
substituted arsonic acids and their salts, esters and amides
substituted benzimidazoles
substituted benzisothiazoles
substituted benzothiadiazinone dioxides
substituted benzoxazines
substituted benzoxazinones
substituted benzothiadiazoles
substituted biurets substituted quinolines
substituted carbamates
substituted aliphatic carboxylic acids and their salts, esters and amides
substituted aromatic carboxylic acids and their salts, esters and amides
substituted carbamoylalkylthiol- or -dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates
substituted dithiophosphoric acids and their salts, esters and amides
substituted ureas
substituted hexahydro-1H-carbothioates
substituted hydantoins
  substituted hydrazides
  substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidine diones
substituted oxadiazine diones
substituted phenols and their salts and esters
substituted phosphonic acids and their salts, esters and amides
substituted phosphonium chlorides
substituted phosphonyalkyl glycines
substituted phosphites
substituted phosphoric acids and their salts, esters and amides
substituted piperidines
substituted pyrazoles
substituted pyrazole alkylcarboxylic acids and their salts, esters and amides
substituted pyrazolium salts
substituted pyrazolium alkyl sulfates
substituted pyridazines
substituted pyridine carboxylic acids and their salts, esters and amides
substituted pyridines
substituted pyridine carboxylates
substituted pyridinones
substituted pyrimidines
substituted pyrimidones
substituted pyrrolidine carboxulic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the active ingredients or compositions thereof according to the invention.

These agents may be added to the herbicides according to the invention in a ratio by weight of from 1 : 10 to 10 : 1. The same applies to oils, fungidcides, nematocides, insecticides, bactericides, antidotes and growth regulators.

The agents according to the invention may be applied, inter alia, once or several times before or after planting, before sowing, preemergence, postemergence, or during emergence of the crop plants and unwanted plants.

EXAMPLE 3

In the greenhouse, the plants rice (*Oryza sativa*), Indian corn (*Zea mays*), soybeans (*Glycine max.*), wheat (*Triticum aestivum*), barnyardgrass (*Echinochloa crus-galli*), annual bluegrass (*Poa annua*), smallflower galinsoga (*Galinsoga parviflora*), common lambsquarters (*Chenopodium album*) and chamomile (*Matricaria chamomilla*) were treated at a growth height of from 2 to 17 cm with 4 kg per hectare of each of the following active inredients, each compound being emulsified or dispersed in 500 liters of water per hectare:

I. 3-(3'-pentyl)-2,1,3-benzothiadiazin-(4)-one-2,2-dioxide
II. 3-(2'-methylbutyl-3')-2,1,3-benzothiadiazin-(4)-one-2,2-dioxide
III. 3-(1'-chlorobutyl-2')-2,1,3-benzothiadiazin-(4)-one-2,2-dioxide
IV. 3-sec-butyl-2,1,3-benzothiadiazin-(4)-one-2,2-dioxide 1-isopropylammonium salt
V. 3-sec-butyl-2,1,3-benzothiadiazin-(4)-one-2,2-dioxide, 1-cyclooctylammonium salt
VI. 3-sec-butyl-2,1,3-benzothiadiazin-(4)-one-2,2-dioxide, 1-n-tridecylammonium salt
VII. 3-sec-butyl-2,1,3-benzothiadiazin-(4)-one-2,2-dioxide, 1-n-undecylammonium salt
VIII. 3-(2'-methylbutyl-1')-2,1,3-benzothiadiazin-(4)-one, 2,2-dioxide, 1-sodium salt
IX. 3-(2'-methylpentyl-4')-2,1,3-benzothiadiazin-(4)-one-2,2-dioxide, 1-sodium salt
X. 3-sec-butyl-2,1,3-benzothiadiazin-(4)-one-2,2-dioxide
XI. 3-(1'-fluoropropyl-2')- and 3-(2'-fluoropropyl-1')-2,1,3-benzothiadiazin-(4)-one-2,2-dioxide
XII. 3-sec-butyl-2,1,3-benzothiadiazin-(4)-one-2,2-dioxide, 1- or 2-(3a,4,5,6,7,7a-hexahydro-4,7-methanoindanyl)ammonium salt (m.p.: 110° to 112° C) and, for comparison,
XIII. 3-methyl-2,1,3-benzothiadiazin-(4)-one-2,2-dioxide XIV. 3-isopropyl-2,1,3-benzothiadiazin-(4)-one-2,2-dioxide.

After 3 to 4 weeks it was ascertained that compounds I to XII had better crop plant compatibility than comparative agents XIII and XIV, combined with the same herbicidal action, especially on grassy weeds.

The results are given below:

| Active ingredient kg/ha | I 4 | II 4 | III 4 | IV 4 | V 4 | VI 4 | VII 4 | VIII 4 | IX 4 | X 4 | XI 4 | XII 4 | XIII 4 | XIV 4 |
|---|---|---|---|---|---|---|---|---|---|---|---|---|---|---|
| Crop plants: | | | | | | | | | | | | | | |
| Oryza sativa | 0 | 0 | 0 | 0 | 0 | 0 | 0 | 0 | 0 | 0 | 0 | 20 | 0 | 0 |
| Zea mays | 0 | 0 | 0 | 0 | 0 | 0 | 0 | 0 | 0 | 0 | 0 | 15 | 0 | 0 |
| Glycine max. | 0 | 0 | 0 | 0 | 0 | 0 | 0 | 0 | 0 | 0 | 0 | 15 | 15 | 0 |
| Triticum aestivum | 0 | 0 | 0 | 0 | 0 | 0 | 0 | 0 | 0 | 0 | 0 | 20 | 0 | 0 |
| Unwanted plants: | | | | | | | | | | | | | | |
| Echinochloa crus-galli | 40 | 80 | 30 | 30 | 35 | 70 | 30 | 25 | 35 | 40 | 30 | 0 | 20 | 25 |
| Poa annua | 40 | 50 | 30 | 30 | 35 | 30 | 25 | 25 | 35 | 40 | 30 | 0 | 20 | 25 |
| Galinsoga parviflora | 90 | 100 | 100 | 100 | 100 | 100 | 100 | 90 | 95 | 100 | 100 | 90 | 100 | 100 |
| Chenopodium album | 100 | 100 | 100 | 100 | 100 | 100 | 100 | 95 | 95 | 100 | 100 | 90 | 100 | 100 |
| Matricaria chamomilla | 100 | 100 | 100 | 100 | 100 | 100 | 100 | 95 | 95 | 100 | 100 | 90 | 100 | 100 |

0 = no damage
100 = complete destruction

EXAMPLE 4

90 parts by weight of compound I is mixed with 10 parts by weight of N-methyl-α-pyrrolidone. A mixture is obtained which is suitable for application in the form of very fine drops.

EXAMPLE 5

20 parts by eight of compound II is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 6

20 parts by weight of compound III is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound IV is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound V is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 9

3 parts by weight of compound VI is intimately mixed with 97 parts by weight of particulate kaolin. A dust is obtained containing 3% by weight of the active ingredient.

EXAMPLE 10

30 parts by weight of compound VII is intimately mixed with a mixture consisting of 92 parts by weight of powdered silica gel and and 8 parts by weight of paraffin oil which has been sprayed onto the surface of this silica gel. A formulation of the active ingredient is obtained having good adherence.

We claim:
1. A compound of the formula

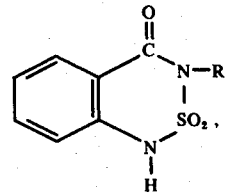

where R sec-butyl or cyclopropyl, or a salt thereof.
2. 3-sec-butyl-2,1,3-benzothiadiazin-(4)-one-2,2-dioxide.

* * * * *